(12) United States Patent
Laghi

(10) Patent No.: US 11,224,527 B2
(45) Date of Patent: Jan. 18, 2022

(54) INTERCHANGEABLE PUMP-LOCK FOR PROSTHETIC SOCKET AND METHOD OF USE

(71) Applicants: Alps South S.R.O., Plezn (CZ); Aldo Laghi, Pinellas Park, FL (US)

(72) Inventor: Aldo Laghi, Pinellas Park, FL (US)

(73) Assignee: Alps South Europe, S.R.O., Plzen (CZ)

( * ) Notice: Subject to any disclaimer, the term of this patent is extended or adjusted under 35 U.S.C. 154(b) by 0 days.

(21) Appl. No.: 16/261,142

(22) Filed: Jan. 29, 2019

(65) Prior Publication Data

US 2019/0231563 A1    Aug. 1, 2019

Related U.S. Application Data

(60) Provisional application No. 62/623,753, filed on Jan. 30, 2018.

(51) Int. Cl.

| A61F 2/78 | (2006.01) |
|---|---|
| A61F 2/80 | (2006.01) |
| A61F 2/68 | (2006.01) |
| A61F 2/50 | (2006.01) |
| A61F 2/74 | (2006.01) |

(52) U.S. Cl.
CPC .................. *A61F 2/80* (2013.01); *A61F 2/68* (2013.01); *A61F 2/78* (2013.01); *A61F 2/742* (2021.08); *A61F 2002/5007* (2013.01); *A61F 2002/5072* (2013.01); *A61F 2002/5083* (2013.01); *A61F 2002/7875* (2013.01); *A61F 2002/802* (2013.01); *A61F 2002/805* (2013.01); *A61F 2002/807* (2013.01)

(58) Field of Classification Search
CPC ........ A61F 2/80; A61F 2/78; A61F 2002/807; A61F 2002/802; A61F 2002/7875
See application file for complete search history.

(56) References Cited

U.S. PATENT DOCUMENTS

| 5,376,129 A | 12/1994 | Faulkner et al. |
| 8,197,555 B2 | 6/2012 | Laghi |
| 9,119,735 B2 * | 9/2015 | Accinni ............... A61B 5/4851 |
| 9,707,107 B2 * | 7/2017 | Ingimarsson ............. A61F 2/80 |

(Continued)

FOREIGN PATENT DOCUMENTS

KR    20130055449 A    5/2013

*Primary Examiner* — Bruce E Snow
(74) *Attorney, Agent, or Firm* — GrayRobinson, P.A.

(57) ABSTRACT

An interchangeable lock-pump prosthetic system that includes a universal dummy, vacuum pump, and mechanical lock. Each of the three objects have similar geometries for the purpose of fitting into a prosthetic, whereupon a user may for instance, swap the vacuum pump with the lock, depending on the needs of the user and without changing to a separate prosthetic. The universal dummy is an inactive component and acts as a placeholder during manufacturing of the socket, for the eventual inclusion of the vacuum pump or mechanical lock. The vacuum pump is a pressure dependent object that acts to remove any residual air between the socket and the elastomeric liner. The lock takes advantage of a mechanical locking pin which receives a properly configured liner, thus securing the user within the prosthetic socket.

11 Claims, 16 Drawing Sheets

(56) References Cited

U.S. PATENT DOCUMENTS

| | | | |
|---|---|---|---|
| 2001/0001837 A1* | 5/2001 | Capper | A61F 2/76 623/34 |
| 2004/0030409 A1 | 2/2004 | Phillips et al. | |
| 2006/0010690 A1 | 1/2006 | Bogue | |
| 2007/0196222 A1 | 8/2007 | Mosler et al. | |
| 2008/0004716 A1 | 1/2008 | Hoerner | |
| 2010/0262261 A1 | 10/2010 | Laghi | |
| 2016/0000586 A1 | 1/2016 | Hurley et al. | |
| 2020/0188141 A1* | 6/2020 | Muller | A61F 2/7812 |

* cited by examiner

INTERCHANGEABLE PUMP-LOCK FOR PROSTHETIC SOCKET AND METHOD OF USE

CROSS-REFERENCE TO RELATED APPLICATIONS

This application claims priority to provisional application No. 62/623,753, filed Jan. 30, 2018, the disclosure of which is incorporated by reference herein.

TECHNICAL FIELD

This disclosure relates to a prosthetic socket and prosthetic socket lock. More specifically, this disclosure relates to a prosthetic socket lock and prosthetic socket vacuum pump set that are constructed to have similar geometry and thereby the same construction dummy for the purpose of providing interchangeability within the same prosthetic socket.

BACKGROUND OF THE INVENTION

Field of the Invention

This invention relates to an interchangeable pump-lock system for a prosthetic socket. More specifically, this invention relates to a system in which a prosthetist may interchange a dummy with either a vacuum pump or a mechanical locking mechanism, thus providing an amputee multiple options when using a prosthetic socket.

Description of the Background Art

Within the field of prosthetics, a variety of locking mechanisms and vacuum pumps exist to secure the amputees' residual limb within a socket. Traditionally, the socket is made from either a thermoplastic or composite material. The process for constructing a socket is labor intensive and complicated and requires extensive training. Prior to socket construction the prosthetist takes into account the device that will be utilized for securing the amputee's residual limb within the socket, whether a vacuum pump or mechanical lock hereinafter "securing device." In some applications, the securing device is molded into the socket. Still in others, a construction dummy, or component without functionality, but having the geometric properties of the securing device, is obtained and used during construction. After construction has been completed the construction dummy is removed and the securing device is installed into the volume created by the dummy.

The majority of prosthetic sockets are constructed to accommodate a mechanical lock. This requires the prosthetist to take into account that the liner required will be a locking liner. Said locking liner having a distal attachment suitable for receiving a threaded pin. The threaded pin has serrations that interfere with the mechanical lock when inserted therein. Said prosthetic assembly, that utilizes a mechanical locking device, is generally more cost effective and easier to use than a prosthetic assembly that utilizes a vacuum pump.

Prosthetic sockets that accommodate a vacuum pump also require the prosthetist to take into account the specific make and model of the vacuum pump that will be utilized for the socket build. Additionally, the prosthetist must take into account the prosthetic liner that will be used. In the case of a socket utilizing a vacuum pump, the liner would not have a mechanical locking device at the distal end.

U.S. Pat. No. 8,197,555 ("'555 Patent") issued to Laghi et al. discloses a vacuum pump of the type listed above and is incorporated by reference herein. However, the '555 Patent does not address the fundamental difficulty of allowing a prosthetist to manufacture a prosthetic that can use either a mechanical locking mechanism or a vacuum pump. Furthermore, the '555 Patent only discloses using an elastomer material for the spring mechanism within the vacuum pump, thus an elastomeric material only allows for a certain volume of air to be present within the vacuum pump versus having a more dense and compressible material, such as a metal, or a more porous material, such as foam.

The fundamental problem is that if a prosthetist builds a socket utilizing a vacuum pump and afterwards determines it is incompatible with the amputee (for any number of reasons), the socket must be rebuilt. Not only is cost a consideration, but patient health becomes a factor as the build time is significant and the patient is generally immobile during that time period. The dilemma can equally be viewed from the other perspective in which a prosthetist builds a socket utilizing a mechanical lock and afterwards determines is incompatible with the amputee for any number of reasons. Again, the socket must be rebuilt.

The present invention overcomes the aforementioned inadequacies by providing the prosthetist with a universally shaped securing device. In other words, the securing device is a vacuum pump and mechanical lock that are geometrically similar so as to be able to interchangeable with another. This allows for a single socket construction to accommodate either securing device.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

For the purpose of summarizing this invention, this invention comprises a interchangeable vacuum pump and mechanical lock securing device for use in prosthetic applications to properly secure the residual limb within the prosthetic socket.

Embodiments of the present invention are herein described by way of example and directed to a interchangeable pump-lock prosthetic securing device. The aforementioned state of the art of prosthetic securing shows the need for improvements, specifically in the ability of the user to switch between a mechanical locking mechanism to a vacuum pump mechanism, depending on the user's needs and applications.

The pump-lock system of the present invention satisfies the aforementioned deficiencies because of its unique, interchangeable design and ability to properly distribute externally applied forces.

Therefore, it is an object of this invention to provide a prosthetic socket that is easily manufactured to use either a mechanical lock or a vacuum pump as the securing means to a prosthetic socket.

Another object of this invention is to provide a construction dummy as a placeholder for the mechanical lock or vacuum pump, with the dummy, lock and pump having similar outer dimensions.

Another object of this invention is to provide a foam/metal spring or cushion for the purposes of having a larger reservoir of air to be used during the pumping action of the user.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present disclosure and its advantages, reference is now made to the following descriptions, taken in conjunction with the accompanying drawings, in which.

Similar reference characters refer to similar parts throughout the several views of the drawings.

DETAILED DESCRIPTION OF THE PREFERRED EMBODIMENT

The following description is of the best mode presently contemplated for carrying out the invention. This description is not to be taken in a limiting sense, but is made merely for the purpose of describing one or more preferred embodiments of the invention. The scope of the invention should be determined with reference to the claims. The various components of the present invention, and the manner in which they interrelate, are described in greater detail hereinafter.

Figure 1:
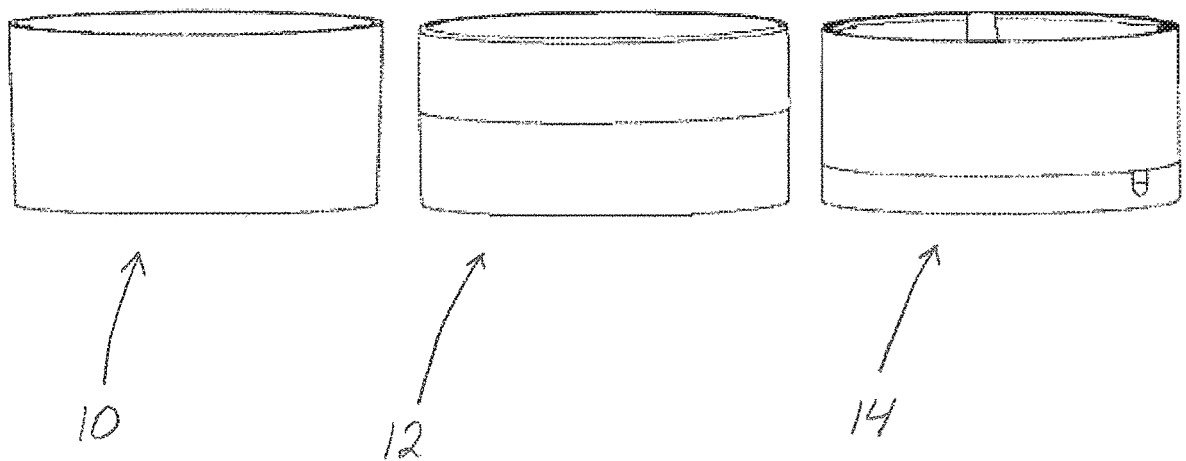
FIG. 1 is a perspective view of the dummy (left), vacuum pump (middle) and mechanical locking device (right)

As shown in FIG. 1, a dummy 10, vacuum pump 12, and mechanical lock 14 each have similar geometries, providing the basis for the invention that each are interchangeable depending on the needs of a user of the prosthetic limb.

Figure 2:
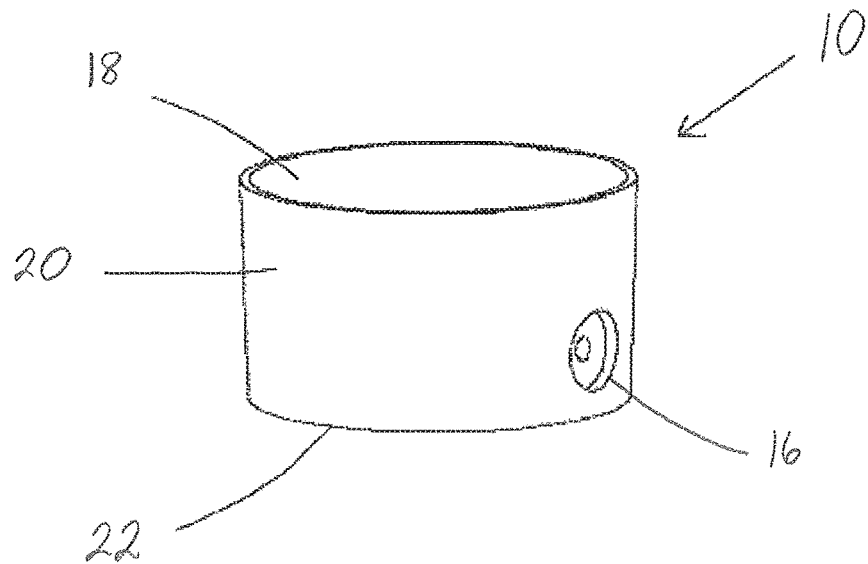
FIG. 2 is a perspective view of the dummy.
Figure 13:
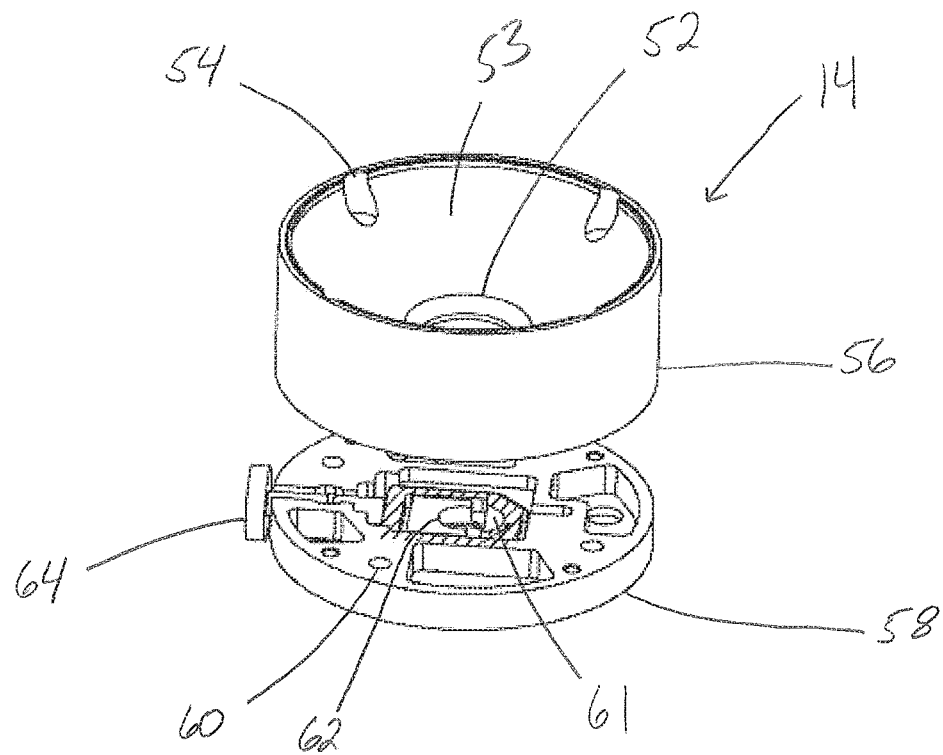
FIG. 13 is an exploded view of the mechanical lock.

As shown in FIG. 2, the dummy 10 has an upper flat surface 18 and a lower flat surface 22 that are in contact with an annularly extending side wall 20. The dummy 10 may be tapered or straight based on vacuum strength desired. During the manufacturing of the socket 70, a prosthetist may firmly position the dummy 10 into the distal end of a socket 71 (FIG. 14) whereupon a pin or other grasping means is inserted into a pin hole 16. The purpose of the pin hole 16 is to provide a channel for an eventual mechanical locking pin 64 (FIG. 13). Thus, once the socket 70 has been molded to the shape of the user's residual limb, the prosthetist may then remove the dummy 10, leaving a void within the distal end 71 of the socket 70 having dimensions similar to either the vacuum pump 12 or the mechanical lock 14.

Figure 3:
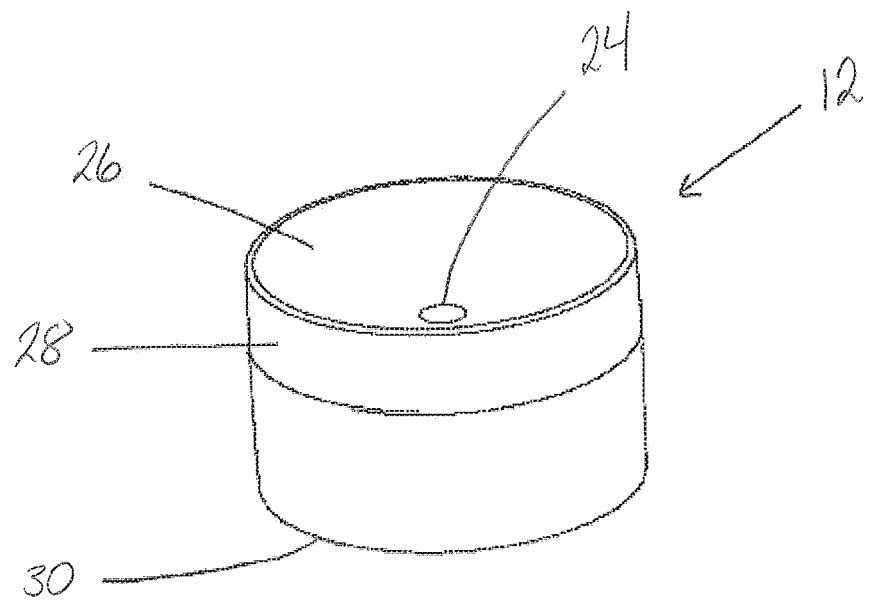
FIG. 3 is a perspective view of the vacuum pump.
Figure 9:
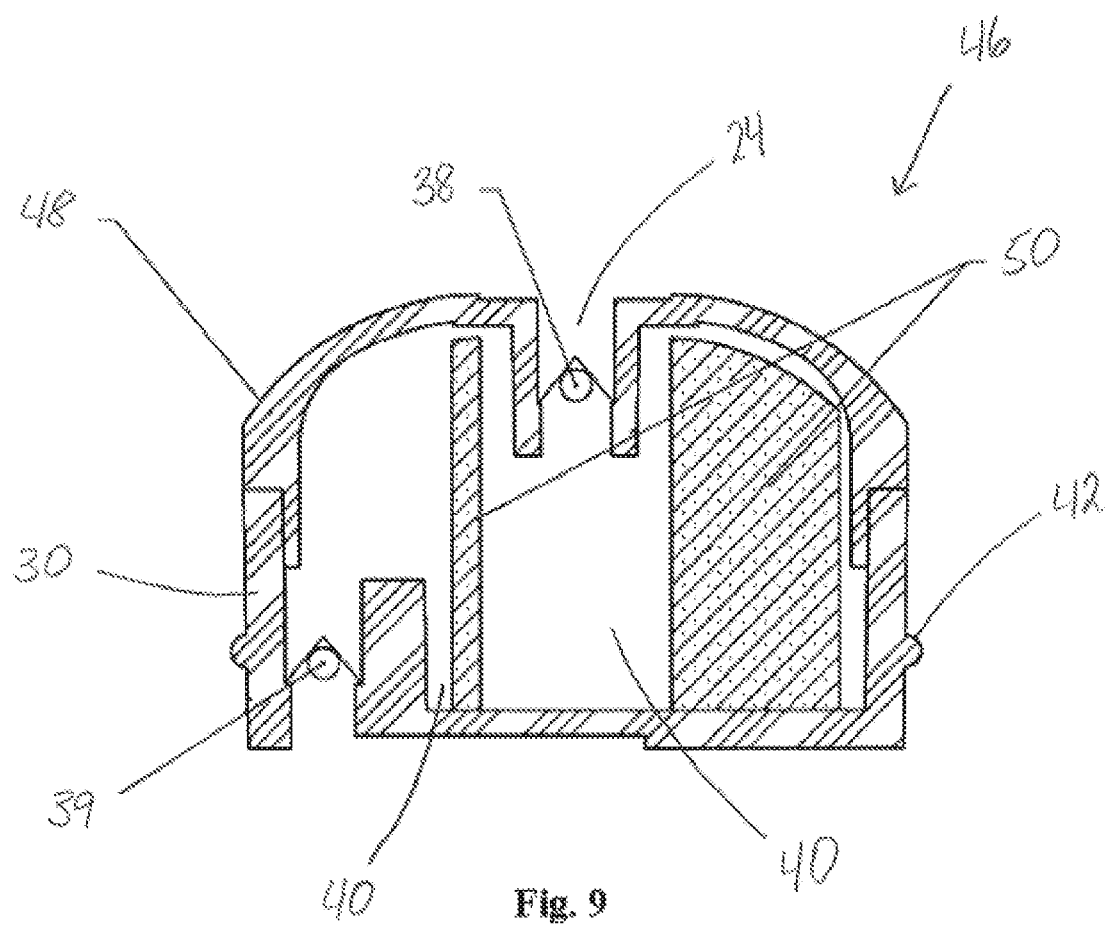
FIG. 9 is a front cross-sectional view of the convex vacuum pump.
Figure 10:
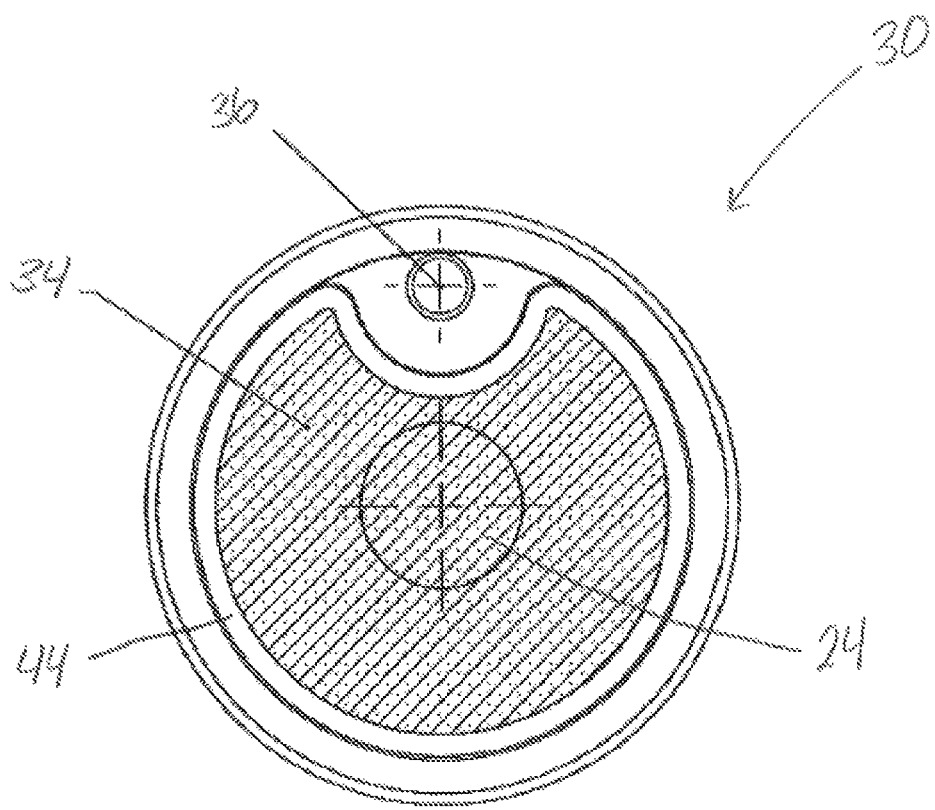
FIG. 10 is a top cross-sectional view of the convex vacuum pump.
Figure 16:
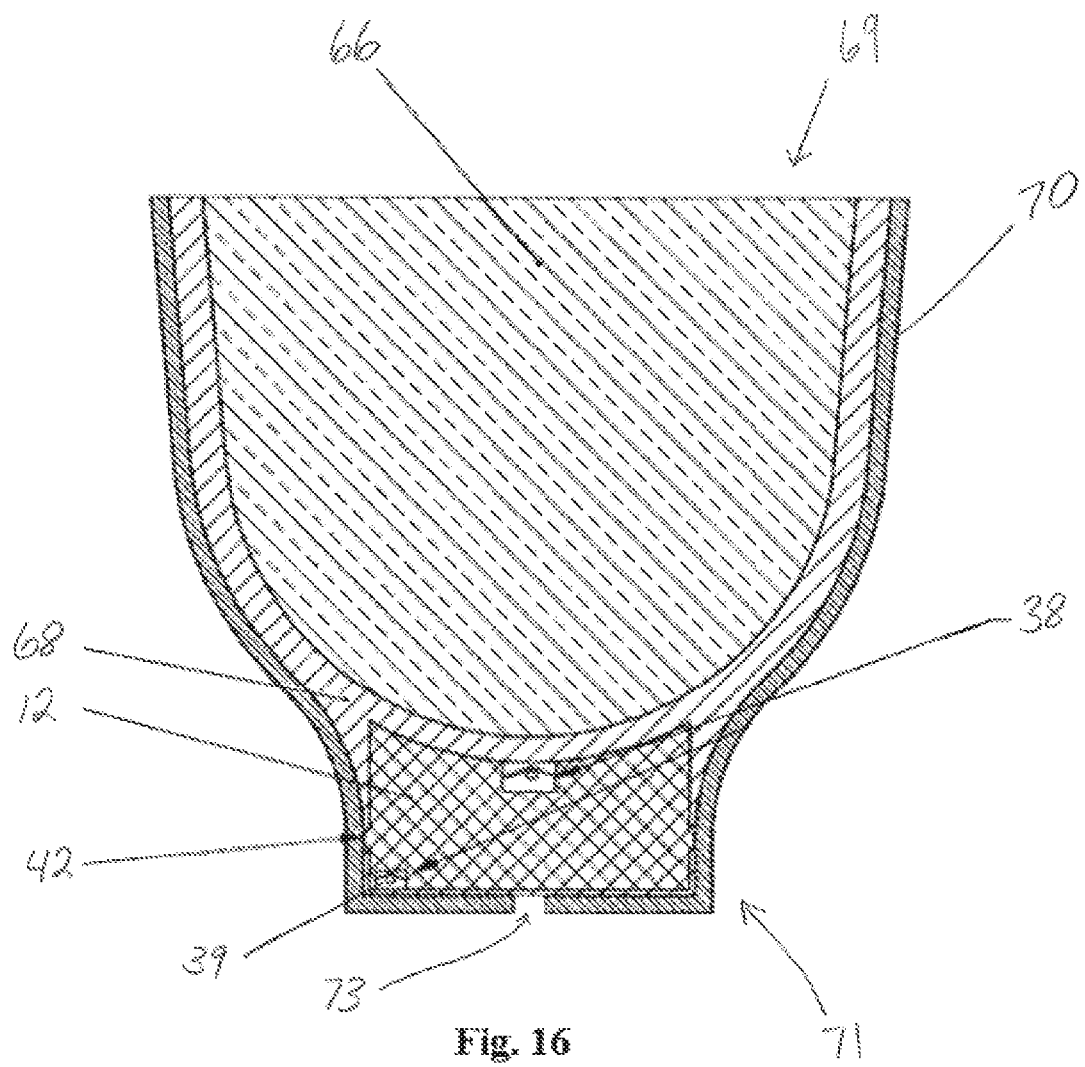
FIG. 16 is a front cross-sectional view of the concave vacuum pump positioned within the liner/socket system, showing the residual air between the liner and socket.

As shown in FIG. 3, the vacuum pump 12 has similar dimensions to that of the dummy 10; however, the vacuum pump 12 can include a concave upper exterior surface 26 that extends conically around the upper portion 28 and down towards the lower portion 30. In another embodiment, the vacuum pump 12 may have a convex upper exterior surface 48 (FIG. 9) in place of the concave upper exterior surface 26. The vacuum pump 12 includes a fluid inlet 24 that receives air from a residual space or vacuum 68 (FIG. 16) between the vacuum pump 12 and socket 70 (FIG. 16). The fluid inlet 24 may have any geometry sufficient to receive fluids such as, circular, square, oval, or any irregular shape with respect to standard geometric shapes. The fluid inlet 24 may also have an attached cover, grate, or filter to provide a means to prevent dust, dirt, or any other foreign substance from entering into the interior of the vacuum pump 12. The fluid inlet 24 may also be located at any point along the concave upper exterior surface 26, depending on the shape of the user's residual limb for the purpose of providing a perfected location at which the user's residual limb seals the fluid inlet 24 during the user's ambulation.

Preferably, the vacuum pump 12 has a housing that is made of an elastomeric material to provide the stretch needed when a user applies pressure during ambulation. Any elastomeric material known or yet to be discovered may be used in the manufacture of the elastomeric housing 72 provided that the proper stretch characteristics are present. This elastomeric housing 72 is the same shape as the dummy 10 to allow for proper fitting by a prosthetist.

Figure 4:
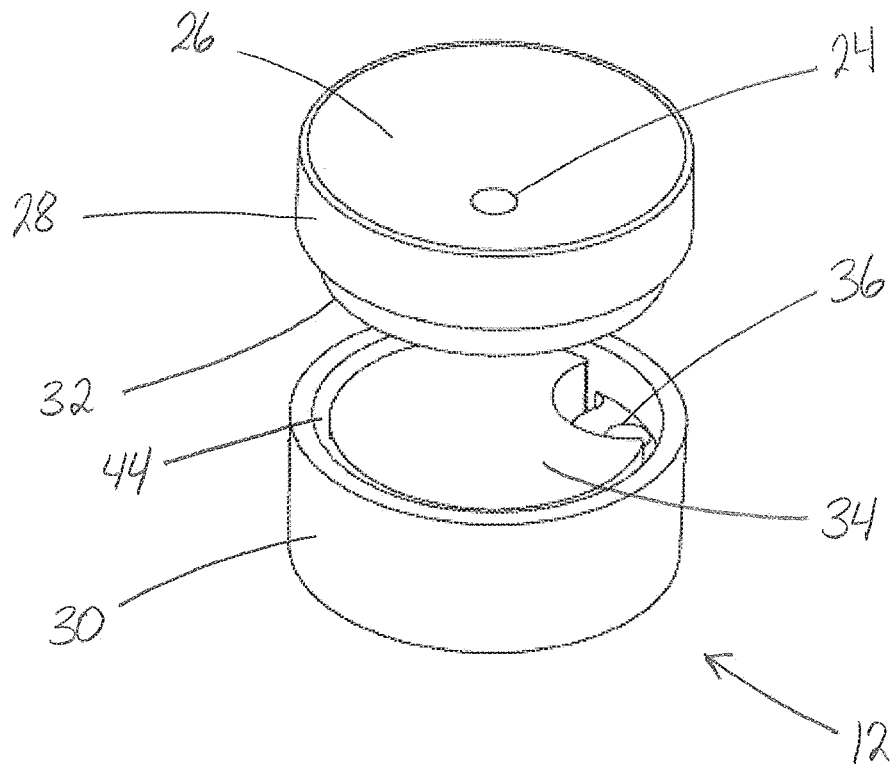
FIG. 4 is an exploded view of the vacuum pump.

As shown in FIG. 4, the upper portion 28 is connected via a male end connector 32 to the lower portion 30 via the outer fluid channel 44. The upper portion 28 may be connected to the lower portion 30 by simply applying any adhesive used in the industry in order to properly seal the interior portion of the vacuum pump 12 from any external factors such as air, dirt, dust, etc. A spring member 34 is disposed within the volume of the lower portion 30 and may be composed of a porous material such as foam, or a material such as a metal or elastomer which does not encompass the entire volume of the lower portion 30, thus allowing fluid to readily circulate throughout the lower portion 30. The spring member 34 may further be either a helical spring or a device that provides an opposing force proportional to the reduction of the overall height of the spring device. Suitable materials for such a device are elastomers, plastics, foam, bladders, and the like. Furthermore, the vacuum pump 12 may be made of any flexible material to allow for deflection while still being rigid enough to remain secure within the socket. In another embodiment, the spring member 34 may be removed entirely and the vacuum pump 12 may act as the spring member provided it is made of material which provides an opposing force proportional to the reduction of the overall height of the vacuum pump 12.

Figure 5:
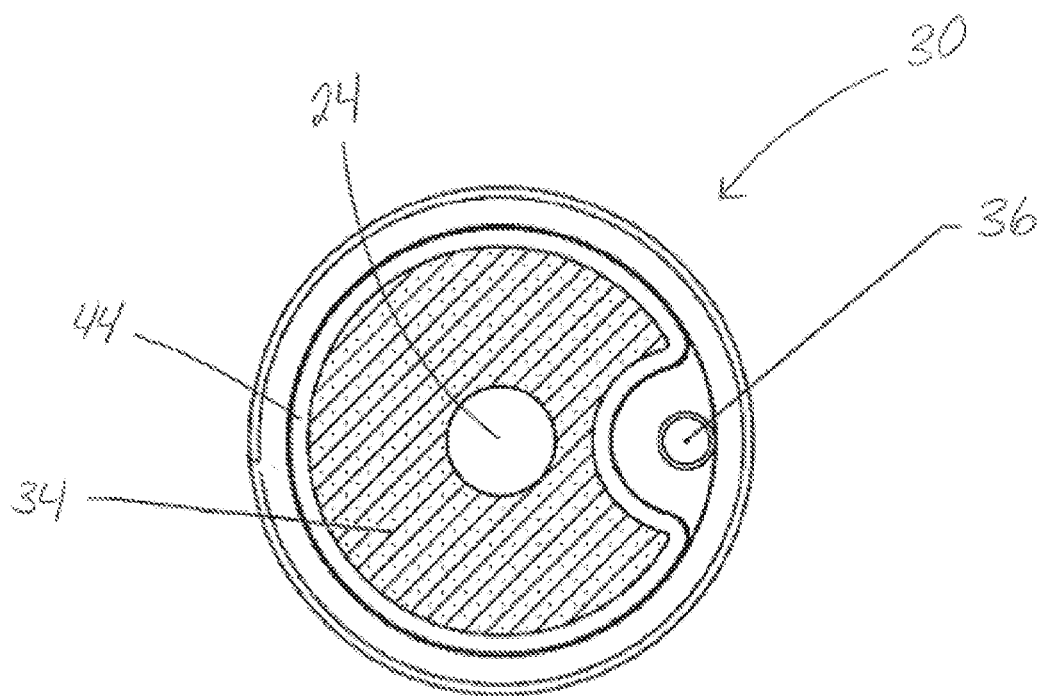
FIG. 5 is a top cross-sectional view of the vacuum pump.
Figure 6:
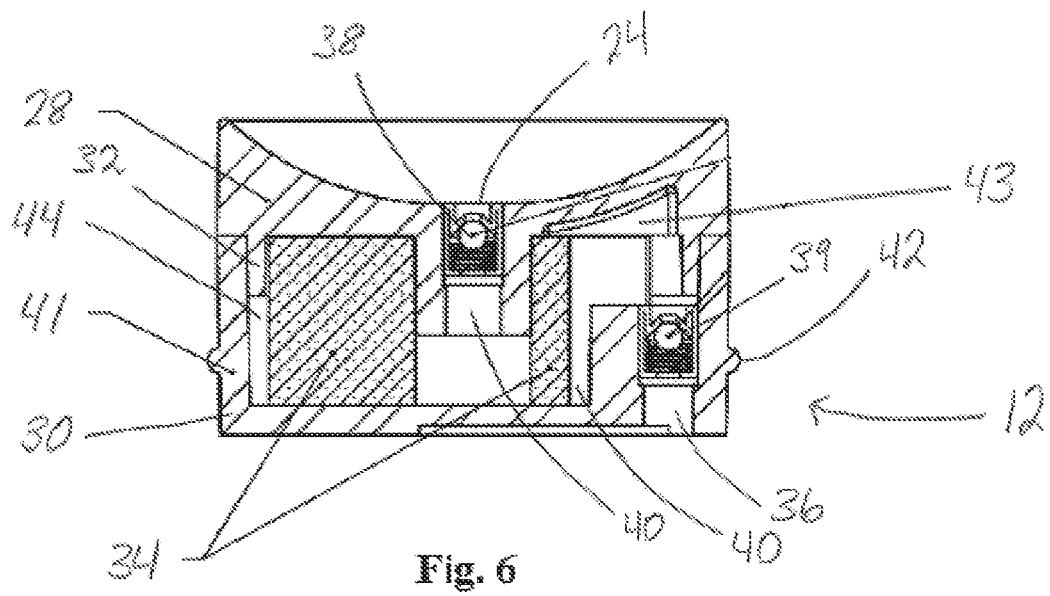
FIG. 6 is a side cross-sectional view of the vacuum pump.
Figure 7:
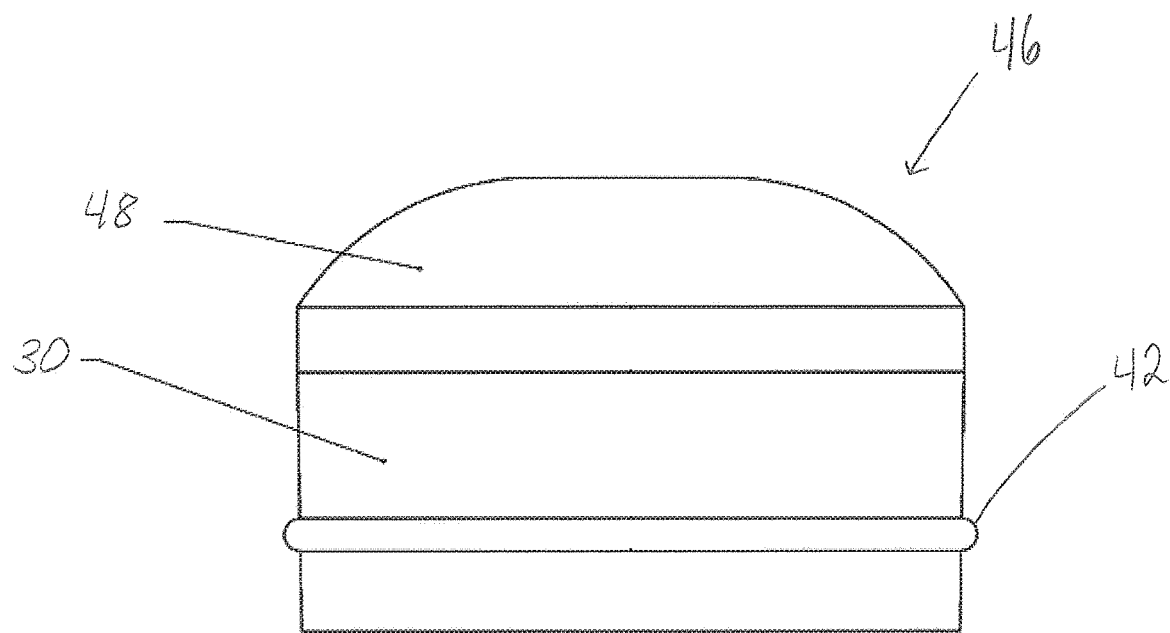
FIG. 7 is a front plan view of the convex vacuum pump.
Figure 8:
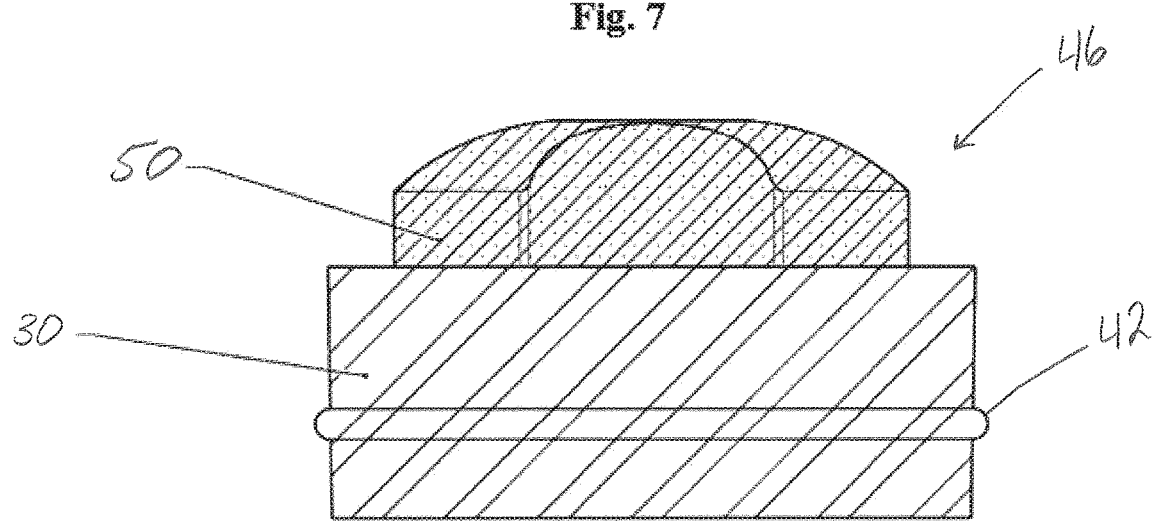
FIG. 8 is a front plan view of the bottom portion of the convex pump in conjunction with a front cross-sectional view of the convex portion of the vacuum pump.

As shown in FIGS. 5 and 6, the vacuum pump 12 includes an upper one-way check valve 38 near the upper portion 28 and a lower one-way check valve 39 near the lower portion 30. The vacuum pump 12 may include more than two valves, depending on the needs of the user such as needing a more flexible vacuum pump 12 to account for varying weights of the user. Sealing element 42 extends annularly relative to the vacuum pump 12 to provide a sealing means between the vacuum pump 12 and the socket 70 (shown in FIG. 16). The sealing element 42 may have widely varying geometries such as, finger-like projections, upwardly or downwardly-extending projections, or any other geometry used to create a seal between the vacuum pump 12 and the socket 70. Moreover, more than one sealing element may be placed as ribs around the vacuum pump 12.

Additionally, the lower portion 30 includes a side wall 41, annularly extending upwards to receive the upper portion 28 via the male end connector 32. The side wall 41 is spaced from the spring member 34 via the outer fluid channel 44, which provides a volume sufficient to receive the male end connector 32. As such, channel 44 acts as a female connector to receive the male end connector 32 of the upper portion 28. The outer fluid channel 44 may have varying dimensions according the manufacturing techniques such that its volume may vary from small to large and may have a conical formation. Although outer fluid channel 44 has a function of allowing male end connector 32 to attach to the lower portion 30, it may also allow fluid flow because its volume is primarily composed of air, as opposed to a porous material such as foam or a dense material such as a metal.

The fluid inlet 24 allows a fluid to enter the interior of the vacuum pump 12 and specifically, the inner fluid channel 40 which is the main conduit to which the fluid is further dispersed either into outer fluid channel 44 or throughout the spring member 34. Once enough pressure has accumulated within the vacuum pump 12, the fluid then exits the vacuum pump 12 via the lower one-way valve 39 and out through the fluid outlet 36. In general, the fluid moving through the fluid inlet is air. FIG. 6 further shows a triangular void 43 that functions to further improve air flow as its volume is primarily composed of air, as opposed to a porous material such as foam or a dense material such as a metal.

As shown in FIGS. 7-10, the system may also incorporate a convex vacuum pump 46 having a convex upper exterior surface 48. The overall design of the convex vacuum pump 46 is identical or substantially similar to that of the vacuum pump 12, except for the dimensions of the convex spring member 50. The convex spring member 50 of the convex vacuum pump 46 has a convex geometry. Thus, the convex spring member 50 extends throughout the interior of the convex vacuum pump 46, excluding the volume encompassed by the fluid channels 40 fluidly connected to the fluid inlet 24.

Figure 11:
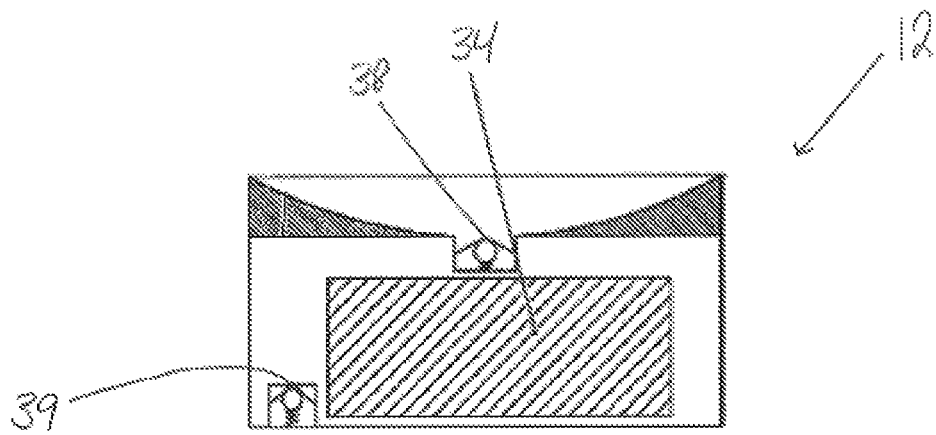
FIG. 11 is a front cross sectional view of the vacuum pump.
Figure 17:
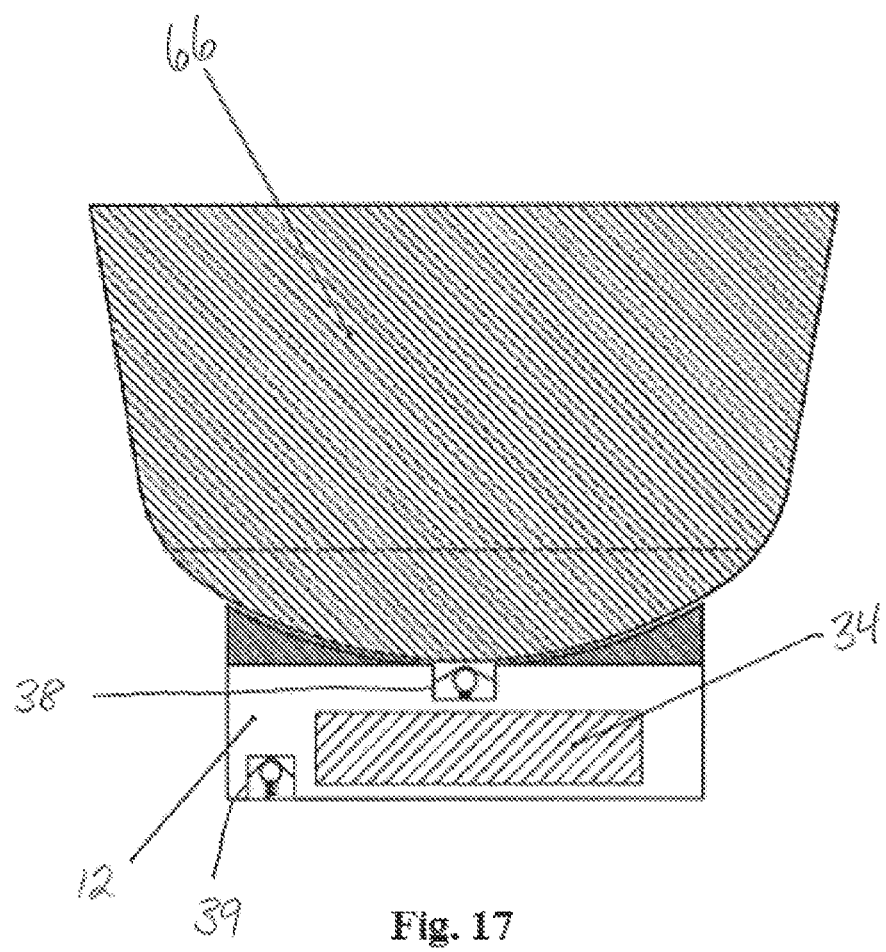
FIG. 17 is a front plan view of the concave vacuum pump positioned relative to the liner with minimal residual air remaining between the two.

As shown in FIG. 11, the spring member 34 is generally positioned within the interior of the vacuum pump 12. Furthermore, this figure is used in FIGS. 16 and 17 to show the placement of the vacuum pump 12 when used in conjunction with the socket 70 (FIG. 16) and liner 66 (FIG. 17).

Figure 12:
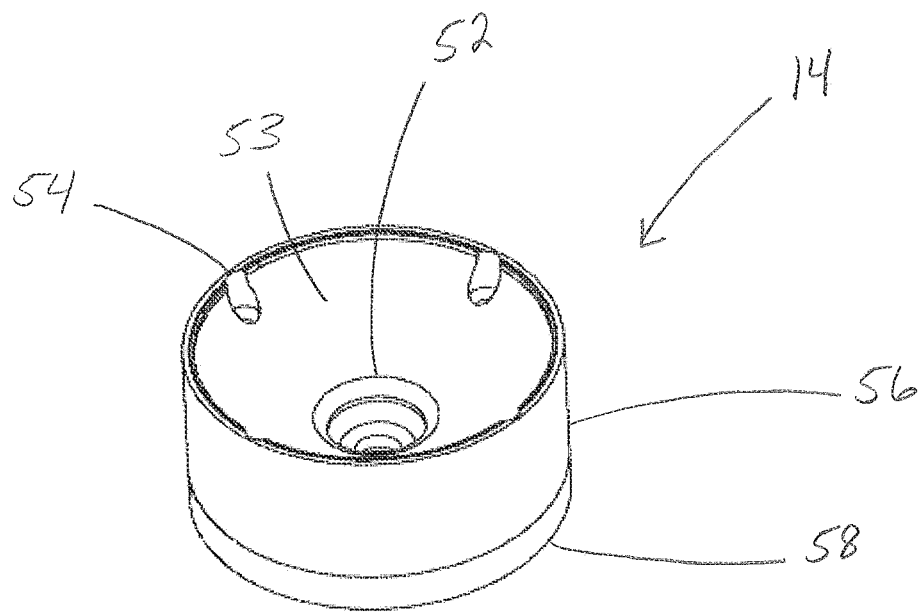
FIG. 12 is a perspective view of the mechanical lock.

As shown in FIG. 12, the system incorporates a mechanical lock 14 which includes an upper portion 56 that has a concave upper surface 53 extending conically down towards a lower portion 58. The upper portion 56 includes an inlet 52 that is configured to receive a male end 76 (FIG. 18) of a liner 72 (FIG. 18) configured to be fitted with the mechanical lock 14. The upper portion 56 additionally includes multiple access points 54 to receive a screw or any other grasping means, to firmly secure the mechanical lock 14 to the socket 70.

As shown in FIG. 13, the lower portion 58 of the mechanical lock 14 further includes a mechanical locking pin 64 that extends laterally within the lower portion 58 to coincide with the distal end 62 of the inlet 52. The mechanical locking pin 64 is configured to extend to the exterior of the socket 70 such that the user may push or press the mechanical locking pin 64 to release the male end 76 of the liner 72 configured to be fitted with the mechanical lock 14. Thus, the mechanical locking pin 64 is configured to be engaged when the male end 76 is fitted within the mechanical lock 14 and disengaged when the male end 76 is absent within the mechanical lock 14. Specifically, a clasping mechanism 61 is removably housed within the distal end 62 of the inlet 52 and functions by grasping the male end 76 when engaged. When the user desires to remove the liner 72 from the mechanical lock 14, the mechanical locking pin 64 is pressed, which disengages the clasping mechanism 61 by sliding the clasping mechanism 61 into the bottom portion 58, thus temporarily removing the clasping mechanism 61 from the distal end 62 of the inlet 52. The lower portion 58 also includes connections 60 for the purpose of using a set screw, rivets, adhesives, or any other grasping means to connect the lower portion 58 to the upper portion 56.

Now that the method of action of the mechanical locking pin 64 has been described, the dummy's 10 pin hole 16 (FIG. 2) can more easily be understood. The purpose of the pin hole 16 is to provide a channel or placeholder for the mechanical locking pin 64. During manufacturing, the manufacturer places a pin or other place-holding means, partially into the dummy 10 and extending to the exterior of the socket 70. Thus, once the manufacturing process of the socket 70 is complete, a channel exists for the mechanical locking pin 64 to extend from the mechanical lock 14 to the exterior of the socket 70, allowing the user to repeatedly push or press the mechanical locking pin 64.

Figure 14:
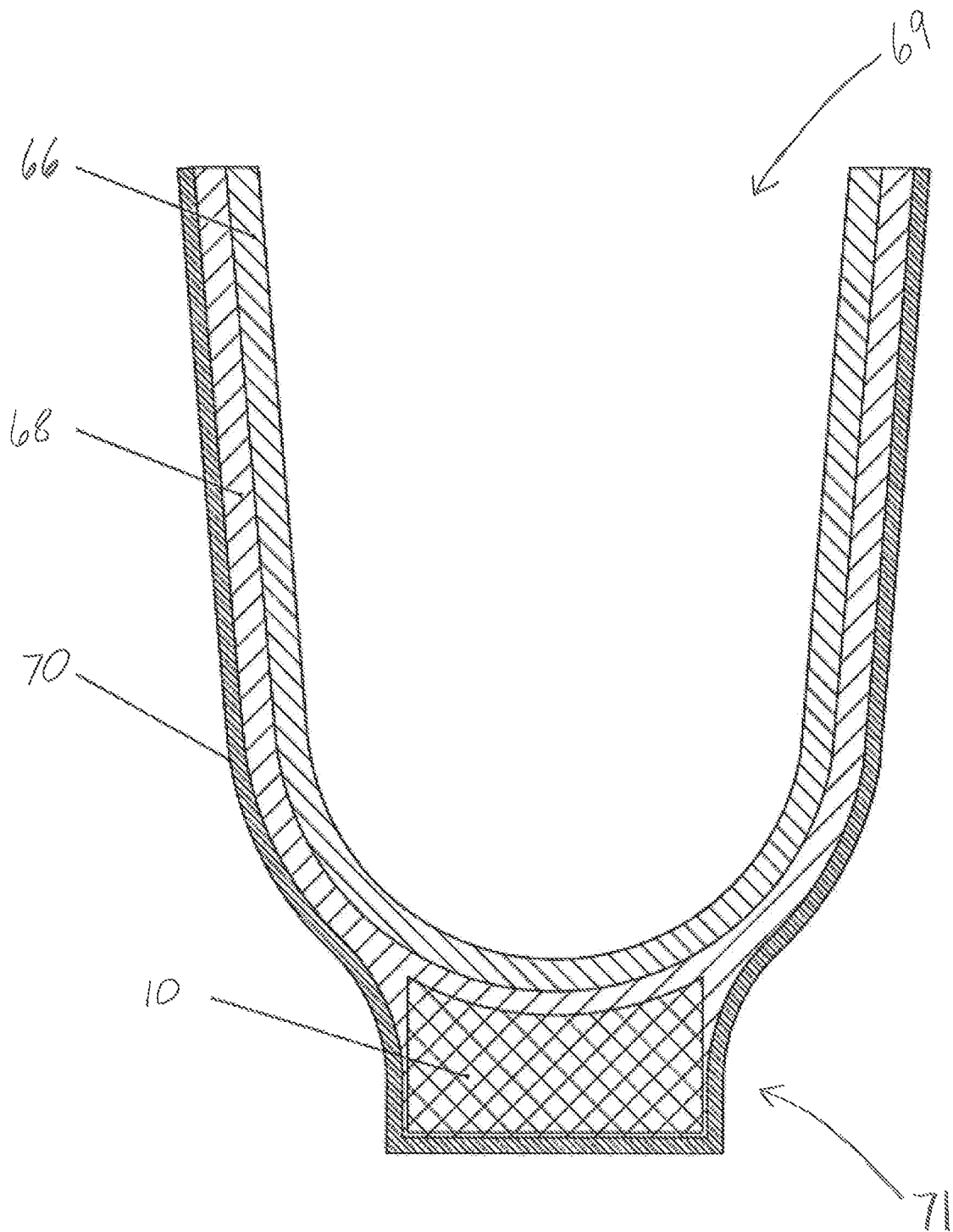
FIG. 14 is a front cross-sectional view of the dummy positioned within the liner/socket system, showing the residual air between the liner and socket.
Figure 15:
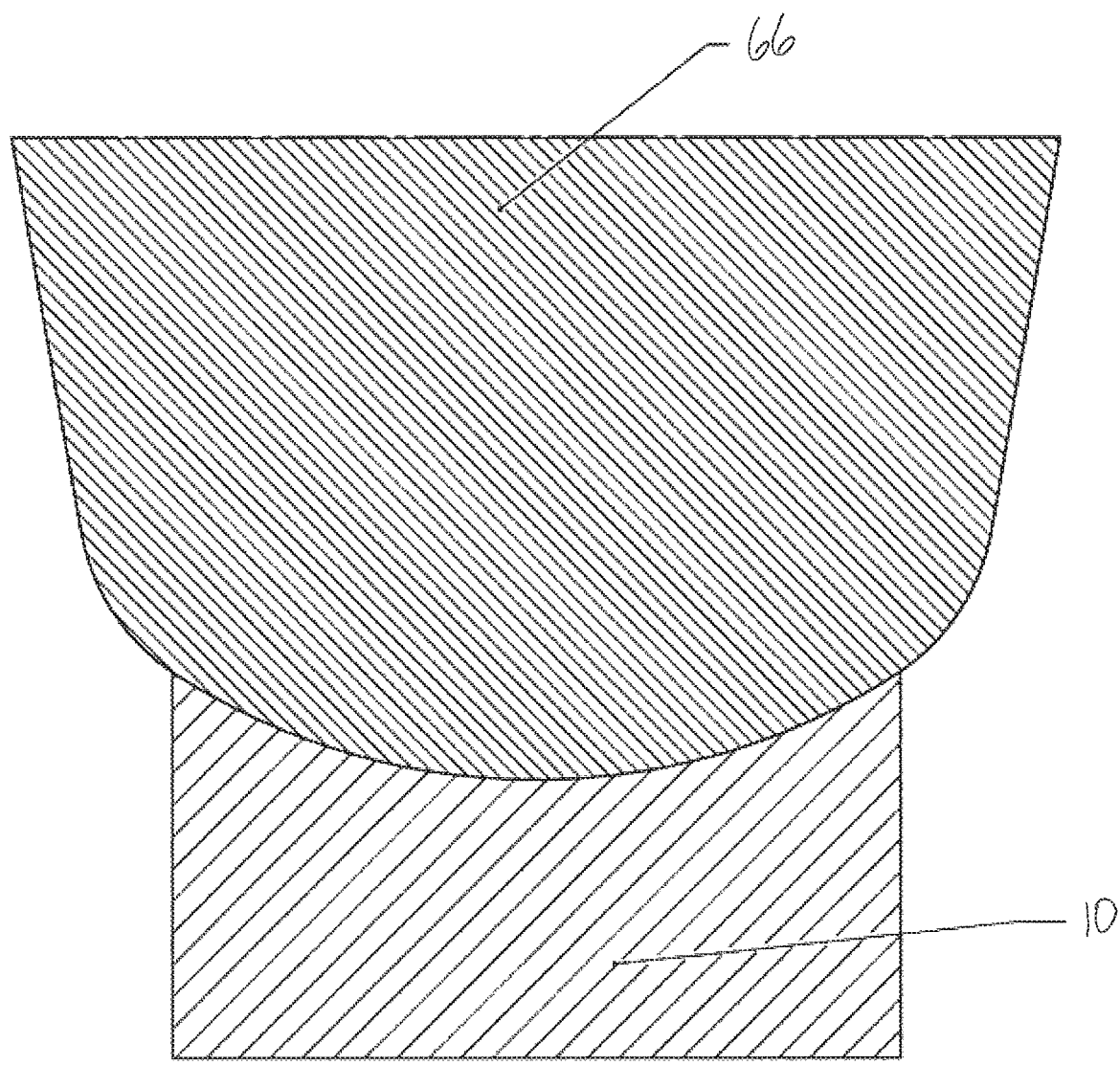
FIG. 15 is a front plan view of the dummy positioned relative to the liner with minimal residual air remaining between the two.

As shown in FIGS. 14 and 15, the dummy 10 is firmly positioned relative to the distal end 71 of the socket 70. Notably, the residual space or vacuum 68 is shown to represent the amount of air between the socket 70 and the liner 66, that exists before the introduction of the vacuum pump 12. In FIG. 15, the dummy 10 is designed to fit in a snug manner to the liner 66.

As shown in FIG. 16, the vacuum pump 12 is incorporated into the distal end 71 of the socket 70 system. The sealing element 42 is shown to represent a seal between the vacuum pump 12 and the socket 70. An outlet 73 coincides with the fluid outlet 36 to provide a means of escape for the discharged fluid from within the vacuum pump 12. As shown in FIG. 17, the vacuum pump 12 is designed to fit in a snug manner to the liner 66.

Figure 18:
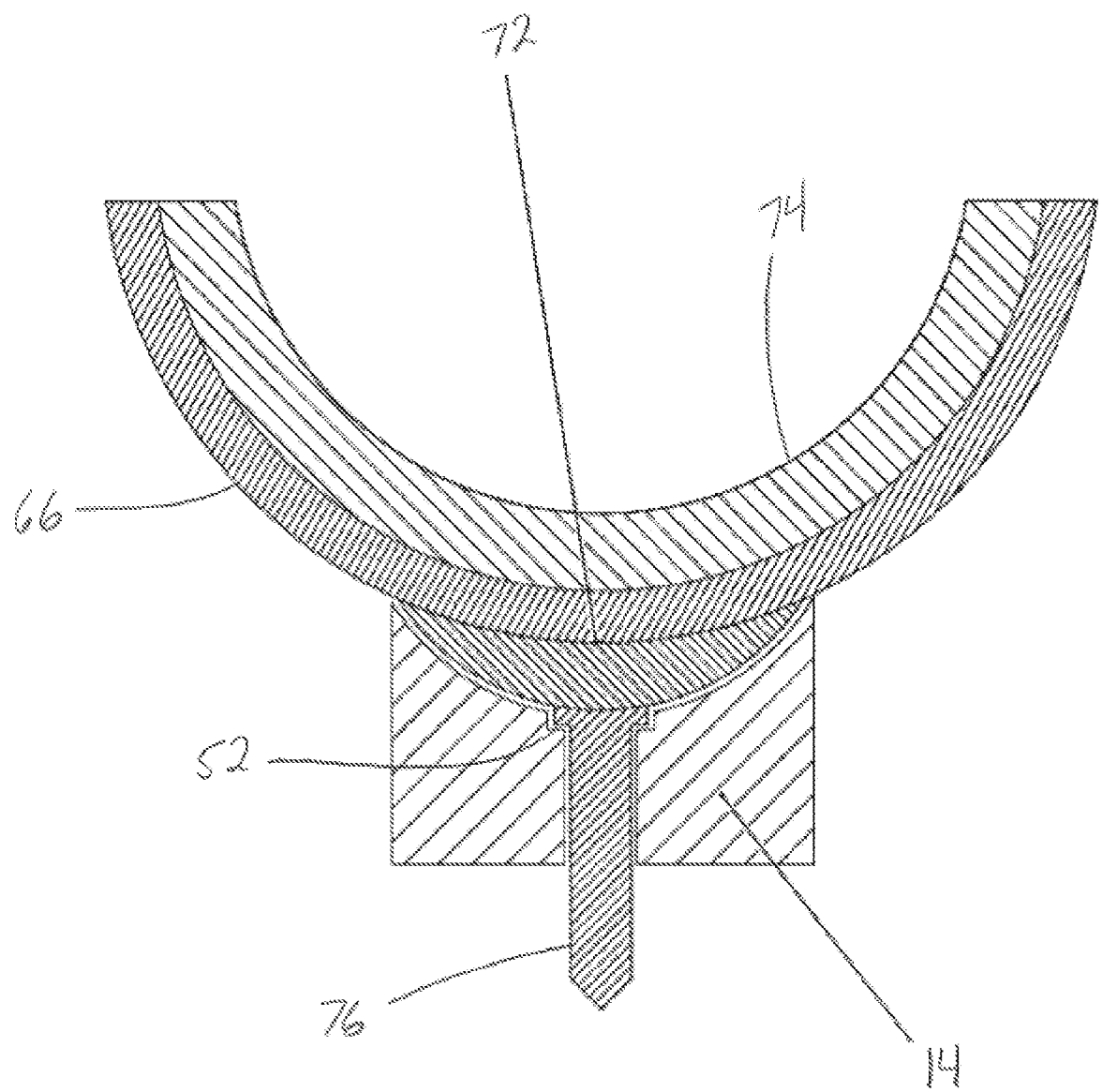
FIG. 18 is a front cross-sectional view of the mechanical lock positioned relative to the liner with minimal residual air remaining between the two.

As shown in FIG. 18, the socket 70 is not shown; however, the mechanical lock 14 is shown for the purposes of showing that the male connector 76 connects relative to the mechanical lock 14 via the inlet 52. As such, once the user dons the liner 66 having mechanical connector 72, the system can then be connected to the mechanical lock 14.

Figure 19:
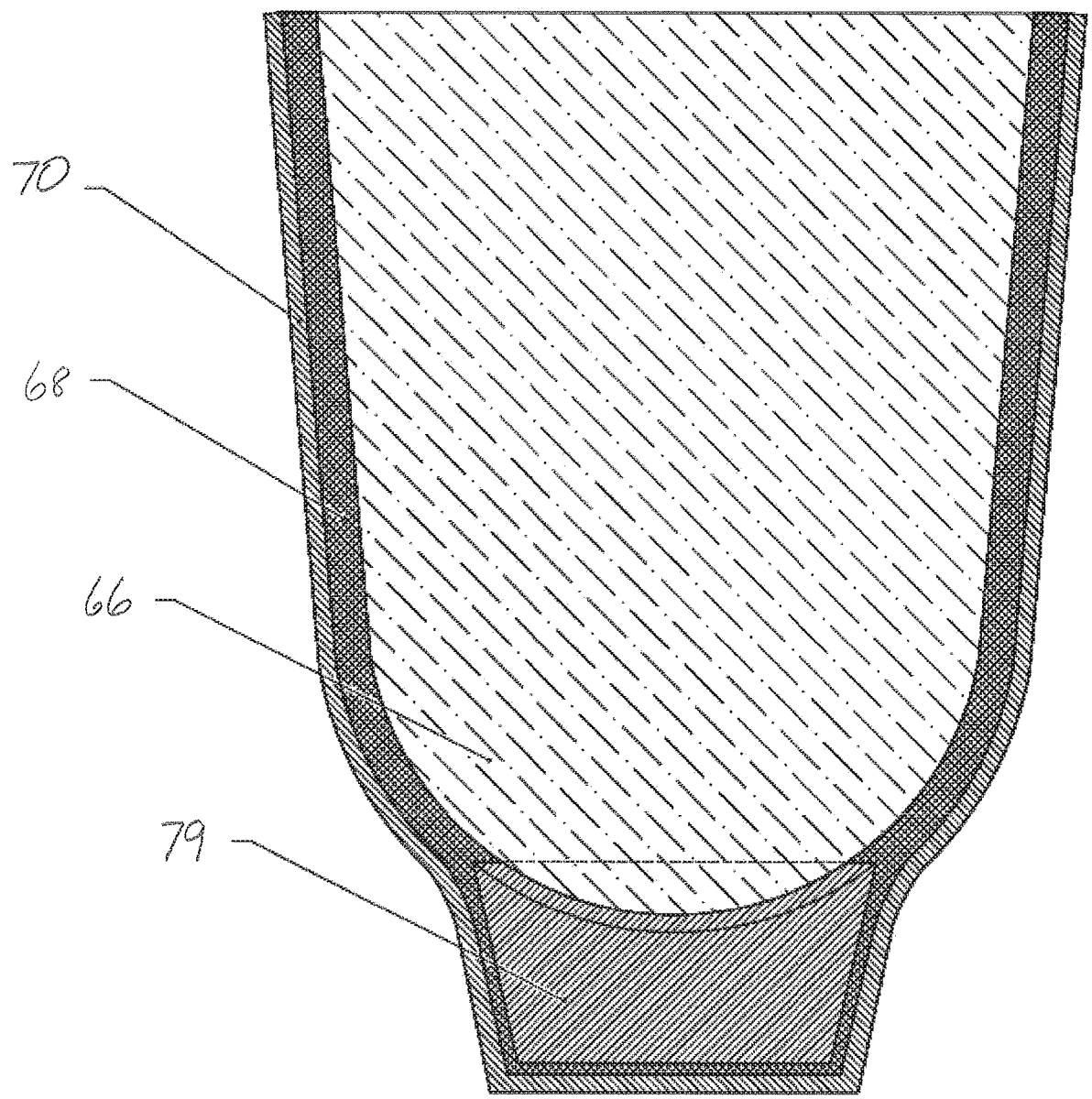
FIG. 19 is a front cross-sectional view of the tapered dummy positioned within the liner/socket system, showing the residual air between the liner and socket.
Figure 20:
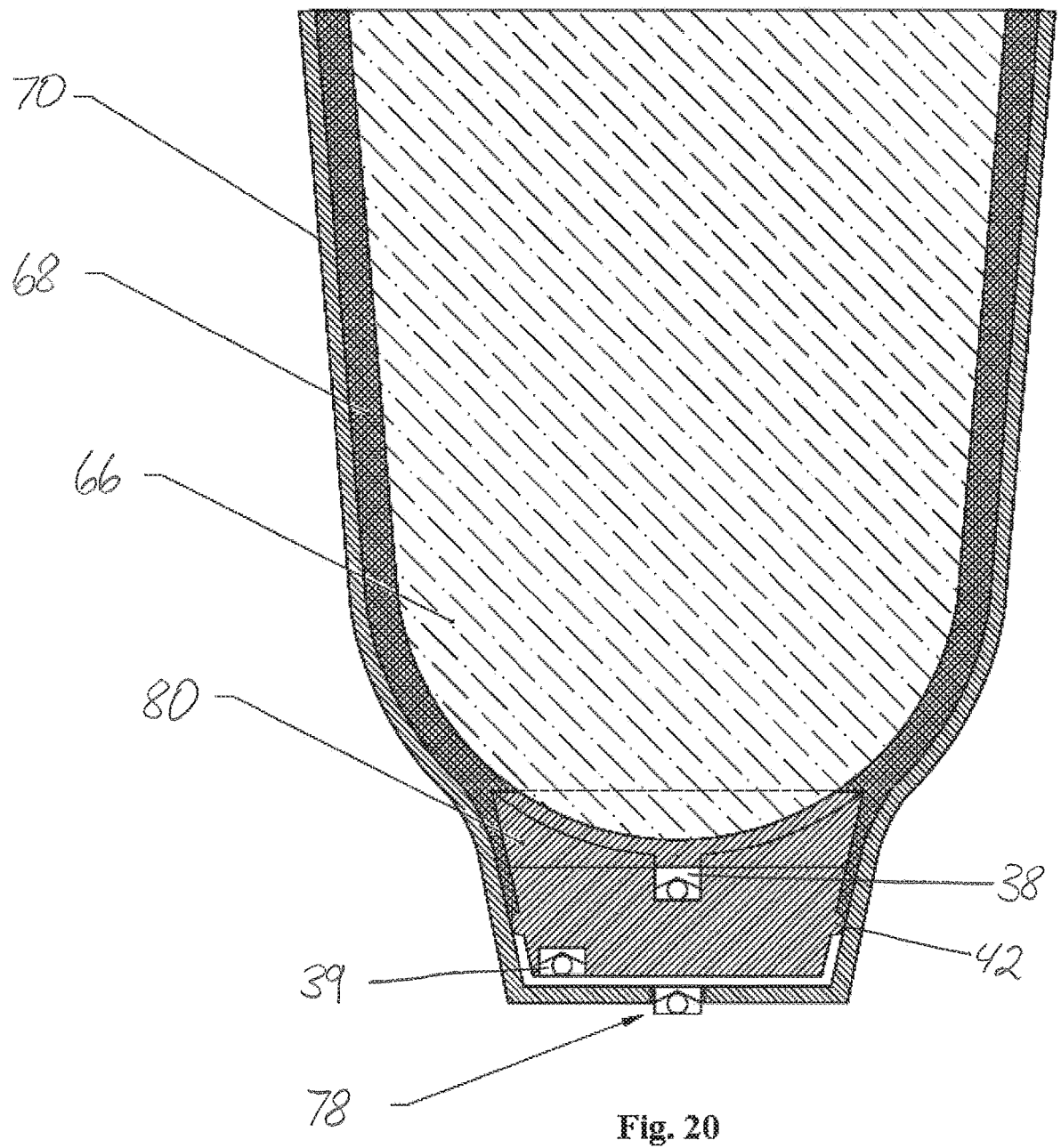
FIG. 20 is a front cross-sectional view of the tapered vacuum pump positioned within the liner/socket system, showing the residual air between the liner and socket.
Figure 21:
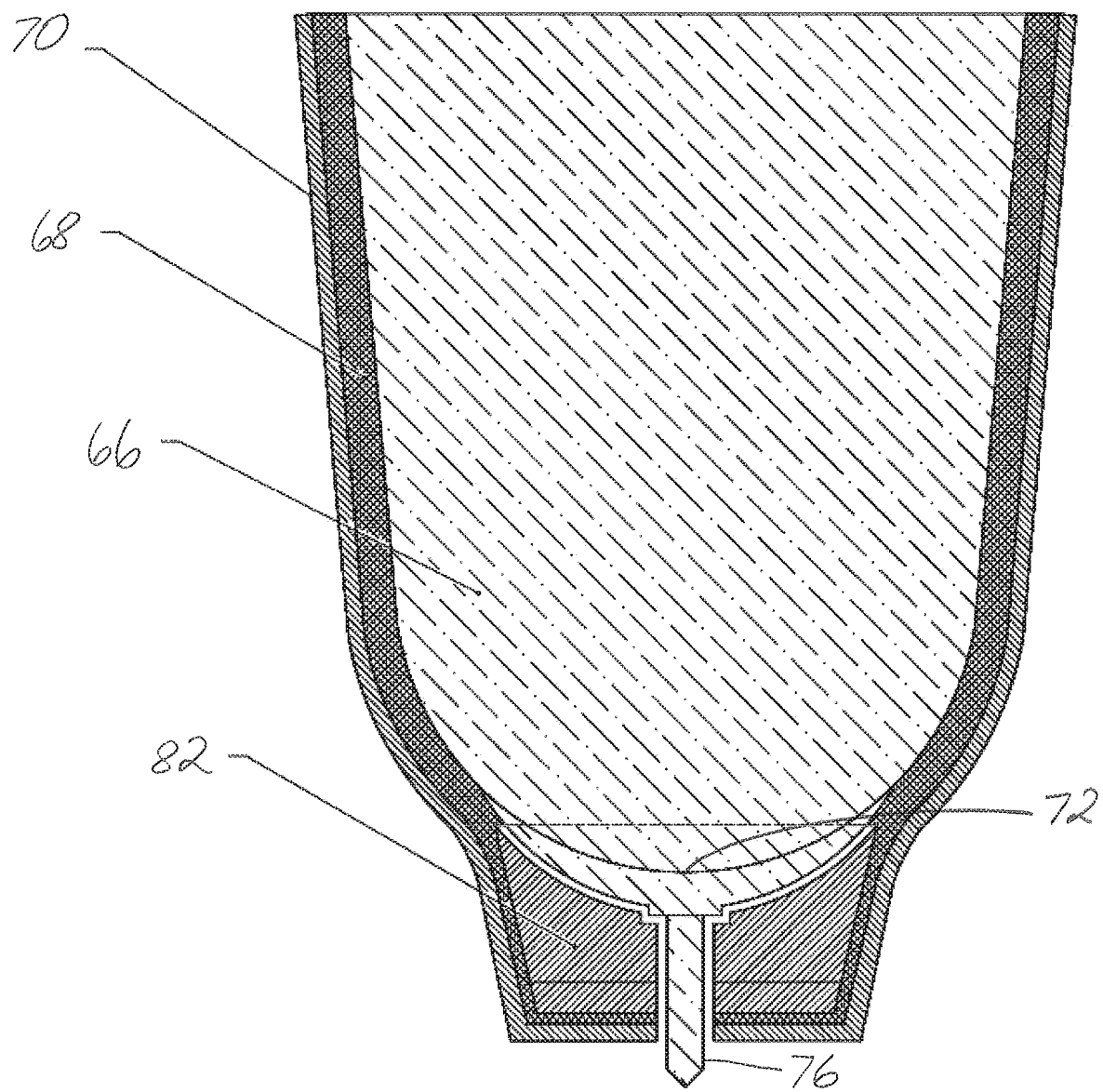
FIG. 21 is a front cross-sectional view of the tapered mechanical lock positioned within the liner/socket system, showing the residual air between the liner and socket.
Figure 22:
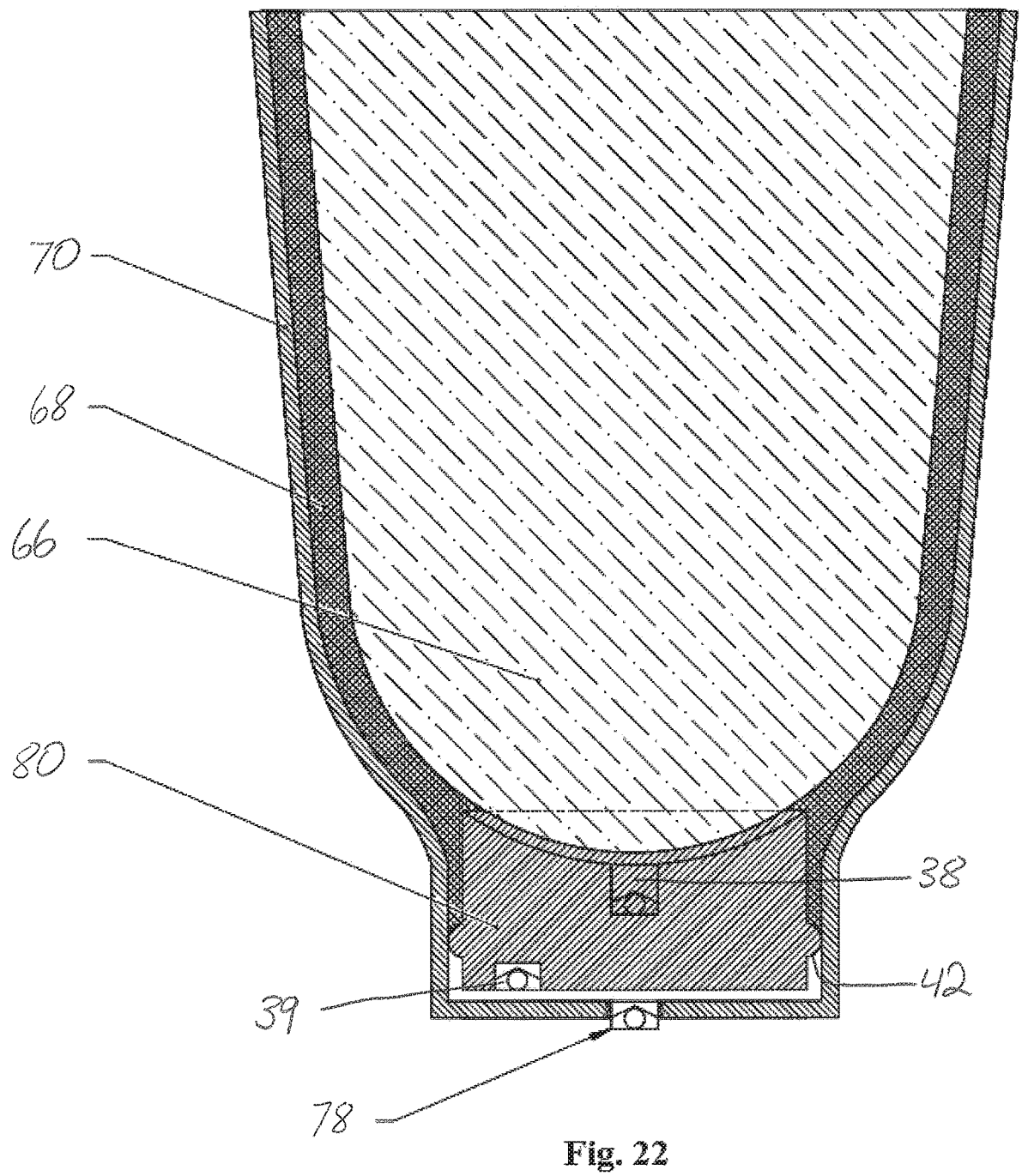
FIG. 22 is a front cross-sectional view of the vacuum pump positioned within the liner/socket system having a one-way valve and also showing the residual air between the liner and socket.

FIGS. 19-22 each show a separate embodiment from the previous figures. Each of the three main components, the dummy 10, vacuum pump 12, and mechanical lock 14 are manufactured such that they have tapered exteriors. For example, FIG. 19 shows a tapered dummy 79 fitted within the distal end 71 of the socket 70. FIG. 20 shows a tapered vacuum pump 80 fitted within the distal end 71 of the socket 70 and furthermore, the distal end 71 of the socket 70 includes a third one-way check valve 78 for purposes of having an increased outlet for any fluid between the socket 70 and liner 66. FIG. 21 shows a tapered mechanical lock 82 that receives the liner 66 having mechanical connector 72. FIG. 22 shows the vacuum pump 12 in a cylindrical configuration fitted within the distal end 71 of the socket 70 and furthermore, the distal end 71 of the socket 70 includes a socket one-way check valve 78 for purposes of having an increased outlet for any fluid between the socket 70 and liner 66. The circumferential shape of vacuum pump 12 may be any geometry that allows for the creation of a level of vacuum 68 and allows the liner 66 to rest. Such geometries include, but are not limited to, circular, hexagonal, and octagonal.

As represented in the above figures, the invention provides a secure connection between the user's residual limb 74 and the socket 70 during the user's ambulation. As such, the cross section and modulus of elasticity of the chosen material used for the vacuum pump 12 determines the spring rate of the vacuum pump 12, which then determines the level of vacuum 68 that will be present between the socket 70 and the liner 66 generated during the user's ambulation. The level of vacuum 68 is important because the secure connection between the socket 70 and the liner 66 is dependent on the level of vacuum 68 present.

Furthermore, the functioning principle of the vacuum pump 12 involve multiple steps, of which include (1) the material within the pump is compressed during the heel strike and the stance phases of the user's gait and (2) then the material returns to a full length during the toe-off and the swing phases of the user's gait. These steps are repeated each full cycle of the user's ambulation and thus, the spring member 34 within the vacuum pump 12 must be rigid yet durable enough to last for many cycles. The level of vacuum 68 achieved during the swing phase of the user's gait is equal to the spring rate multiplied by the length of the achieved compression and collectively divided by the cross sectional area of the vacuum pump 12.

More specifically, after the socket is fully donned by the user and as the user begins to ambulate, with the initial downward step, the downward force of the residual limb within the socket will force any remnant air within the lower section of the socket out through fluid inlet 24 (FIG. 6), through the upper one-way valve 38, into the fluid channel 40 and out through the lower one-way valve 39 while simultaneously compressing the spring member 34 downwardly. As the user lifts his limb off the ground for the next step, the spring member 34 expands causing lower one-way valve 39 to close and upper one-way valve 38 to open and draw more air from within the socket 70 in the fluid channel 40. As the user takes the next step, causing spring member 34 to compress again, the air pressure in fluid channel 40 causes lower one-way valve 39 to open while maintaining upper one-way valve 38 closed thereby relieving air from within fluid channel 45 to be vented through fluid outlet 36. The cycle is repeated as the user ambulates creating a continuous evacuation of air from within the socket.

Moreover, many pumps in the industry have been manufactured to include elastomeric springs or cushions; however, metal springs are either equivalent or more efficient due to their density. That is, since the metal springs are denser (requiring less volume) than elastomeric springs or cushions, air may travel more readily throughout the pump, thus providing a more fluid pumping action within the pump and therefore, a more comfortable experience for the user. The metal springs have a spring rate, or pumping action, determined by the shape of the coils, the Young's modulus of the metal used, and the thickness of the wire that is used to make the coils. Thus, the character of the metal spring is determined from its material and construction.

The spring rate for either elastomeric springs, metal springs, or foam cushion is determined by the cross sectional area of the material multiplied by the modulus of elasticity of the material. The number of steps required to reach steady state of the vacuum pump 12 (or the state at which the user's limb is securely attached within the socket 70) is a function of (1) the free volume of the socket, (2) the required vacuum level (varying from 5 to 20 inches Hg, preferably 5 to 10 inches Hg), and (3) the volume of air that is displaced inside the pump during the stance aspect of the user's gait (the volume displaced for a given pump geometry is directly proportional to the compression allowed during the stance phase, the length of compression is fixed by the height ratio of the pump at rest versus the length of the dummy 10 and has values ranging from 3 to 20 mm and preferably 7 to 8 mm).

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. A method of configuring an assembly to be fitted to an amputee comprising:
   molding a distal end of a prosthetic socket to a removable dummy;
   removing the dummy from the distal end of the prosthetic socket and interchangeably inserting a vacuum pump and a locking mechanism at the distal end, wherein the vacuum pump comprises:

an elastomeric housing comprising an inner fluid channel, an upper exterior surface, and an exterior sealing element;

a spring member, a first one-way valve preventing backflow of air, a second one-way valve preventing backflow of air, wherein the spring member, first one-way valve, and second one-way valve are disposed within the inner fluid channel;

and the locking mechanism comprises:

a mechanical lock having a central inlet and a mechanical locking pin configured to engage a male end of a prosthetic liner when inserted into the central inlet.

2. The method of claim 1 wherein the dummy is cylindrical.

3. The method of claim 1 wherein the dummy is tapered.

4. The method of claim 1 wherein the upper exterior surface is concave.

5. The method of claim 1 wherein the upper exterior surface is convex.

6. The method of claim 1 wherein the spring member comprises a metal.

7. The method of claim 1 wherein the spring member comprises a foam.

8. The method of claim 1 wherein the spring member comprises an elastomer.

9. The method of claim 1 wherein the second one-way valve forces air to flow through a third one-way valve positioned in the prosthetic socket.

10. The method of claim 1 wherein the elastomeric housing is tapered.

11. A method of configuring an assembly to be fitted to an amputee comprising:

molding a distal end of a prosthetic socket to a removable dummy;

removing the dummy from the distal end of the prosthetic socket and interchangeably inserting a vacuum pump and a locking mechanism, the vacuum pump comprising:

an elastomeric housing comprising an inner fluid channel and an upper exterior surface, wherein the elastomeric housing further comprises an elastomer that allows between about 3 and 20 millimeters of compression during a stance phase of ambulation;

a spring member, a first one-way valve preventing backflow, a second one-way valve preventing backflow, wherein the spring member, first one-way valve, and second one-way valve are disposed within the inner fluid channel;

and the locking mechanism comprising:

a mechanical lock having a central inlet and a mechanical locking pin configured to engage a male end of a prosthetic liner when inserted into the central inlet.

* * * * *